US00PP07890P

United States Patent [19]

Zaiger et al.

[11] Patent Number: Plant 7,890

[45] Date of Patent: Jun. 23, 1992

[54] NECTARINE TREE "EASTERN GLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 633,413

[22] Filed: Dec. 21, 1990

[51] Int. Cl.[5] ..... A01H 5/00

[52] U.S. Cl. ..... Plt./41

[58] Field of Search ..... Plt./41

*Primary Examiner*—James R. Feyrer

[57] ABSTRACT

A new and distinct variety of nectarine tree having the following unique combination of desirable features:

1. Early maturity of high color fruit.
2. Fruit with good flavor and eating quality.
3. Heavy and regular production of large size fruit.
4. Fruit with firm flesh, good handling and shipping quality.
5. A wide range of adaptability producing high quality fruit on both fruit growing areas of the West and East Coast of the United States.
6. Relatively uniform ripening of fruit throughout the tree.

1 Drawing Sheet

ORIGIN OF THE VARIETY

The present new and distinct variety of nectarine tree was developed in the experimental orchard located near Modesto, Calif., as a second generation seedling from a cross between Red Grand Nectarine (U.S. Plant Pat. No. 1,060) and Crimson Gold Nectarine (U.S. Plant Pat. No. 2,825). A large group of second generation seedlings were grown and maintained by us which gave a wide range of varying characteristics. One such seedling having especially desirable fruit characteristics was selected for asexual reproduction and commercialization.

ASEXUAL REPRODUCTION OF THE VARIETY

Asexual reproduction of the new nectarine variety by budding was performed by use in our experimental orchard located near Modesto, Calif., and shows that all characteristics of the original tree run true and are established and transmitted through succeeding propagations.

SUMMARY OF THE VARIETY

A new and distinct variety of nectarine tree of large size, vigorous upright growth and is a heavy and regular producer of early maturing, large size, yellow flesh, clingstone fruit with good flavor and eating quality. The fruit is further characterized by having an attractive red skin color, firm flesh with good shipping and storage quality. In comparison to Red Grand Nectarine (U.S. Plant Pat. No. 1,060) the fruit of the new variety matures approximately 5 weeks earlier, and the fruit and its leaves are more resistant to "bacterial spot" caused by *Xanthomonas pruni.* In comparison to Crimson Gold Nectarine (U.S. Plant Pat. No. 2,825) the fruit of the new variety is larger in size with more uniform size of fruit throughout the tree and ripens approximately 7 days later.

BRIEF DESCRIPTION OF THE PHOTOGRAPHS

The accompanying photographic illlustrations show typical specimens of the foliage and fruit of the present new nectarine variety, with the upper and lower surface of the leaves being illustrated, with an exterior and sectional view of the fruit to reveal flesh coloration with a stone remaining in place. The photographic illustrations were take shortly after the fruit was picked at maturity (firm ripe) and the colors are as nearly true as is reasonably possible in a color representation of this type.

DESCRIPTION OF THE VARIETY

The botanical detailed description of the present variety of nectarine tree, its flowers, fruit and foliage, is based on observations of the specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Shape.*—Normally pruned to vase shape.
- *Production.*—Productive.
- *Bearer.*—Regular.

Trunk:
- *Size.*—Large, stocky.
- *Texture.*—Medium shaggy.
- *Color.*—Brown to grayish brown.

Branches:
- *Size.*—Medium to large.
- *Texture.*—Smooth to medium rough.
- *Color.*—Reddish brown to brown.
- *Lenticels.*—Large size. Numerous.

Leaves:
- *Size.*—Large. Average length — 7". Average width — $1\frac{1}{2}$".
- *Form.*—Lanceolate.
- *Margin.*—Crenate.
- *Texture.*—Smooth.
- *Thickness.*—Medium.
- *Petiole.*—Medium length — average $\frac{7}{8}$". Medium thickness — average 1/16".
- *Glands.*—Reniform. Number varies from 1 to 4. Average number 2. Medium size. Usually located on lower portion of leaf blade — occasionally on upper portion of petiole.

Flower Buds:

*Size.*—Large.
*Length.*—Medium.
*Form.*—Plump.

Flowers:

*Blooming period.*—Date of first bloom — Mar. 3, 1990. Date of last bloom — Mar. 10, 1990. Varies slightly with climatic conditions.
*Pollen.*—Present. Self fertile.
*Color.*—Pink.

Fruit:

*Maturity when described.*—Firm ripe.
*Date of first picking.*—Jun. 7, 1990.
*Date of last picking.*—Jun. 13, 1990.
*Size.*—Large. Average diameter axially —2¾". Average transversely in suture plane — 2⅝".
*Form.*—Nearly globose — slightly elongated in suture plane.
*Suture.*—Shallow but distinct, extends from base through apex.
*Ventral surface.*—Varies from rounded to slightly lipped.
*Cavity.*—Rounded to slightly elongated in suture plane. Average depth — ⅝". Average breadth — ⅝".
*Base.*—Retuse.
*Apex.*—Varies from slight point to slight depression.

Skin:

*Thickness.*—Medium.
*Texture.*—Medium to tough. Tenacious to flesh.
*Tendency to crack.*—Very slight.
*Down.*—Wanting.
*Color.*—Yellow ground color (5-A-7 to (5-A-8). Overspread wth red (9-A8) to (9-C-8).

Flesh:

*Ripens.*—Unfirom — only very slightly earlier near apex.
*Texture.*—Firm, meaty.
*Juice.*—Moderate.
*Fibers.*—Few, tender.
*Amygdalin.*—Wanting.
*Aroma.*—Very little.
*Flavor.*—Mild — good balance between sugar and acid.
*Eating quality.*—Good.
*Color.*—Yellow to golden yellow (4-A6) to (5-A-6). Some fruit have slight flecks of red (9-A-7) in flesh just above apex of stone.

Stone:

*Type.*—Clingstone.
*Size.*—Large. Average length — 1½". Average width — 11/16". Average thickness — ⅝".
*Form.*—Oval.
*Base.*—Straight to oblique.
*Apex.*—Acute.
*Sides.*—Equal to unequal.
*Surface.*—Furrowed toward apex, pitted toward base.
*Ridges.*—Rounded toward apex.
*Tendency to split.*—Very slight.
*Color.*—Light brown to brown (8-B-5) to (8-C-6).

Use: Dessert. Local and long distant markets.
Keeping Quality: Good.
Shipping Quality: Good.

The present nectarine tree, its flowers and fruit herein described may vary in slight detail due to different climatic, soil and cultural practices under which the variety may be grown. The description is that of the variety produced under ecological conditions prevailing near Modesto, Calif.

We claim:

1. A new and distinct variety of nectarine tree substantially as illustrated and described, characterized by its large size, vigorous upright growth, with the adaptability to be a productive and regular bearer of fruit in both fruit growing areas located on the West and East Coast of the United States producing large size, firm, yellow flesh, clingstone fruit with good flavor and eating quality; in comparison to its maternal parent Red Grand Nectarine (U.S. Plant Pat. No. 1,060) the fruit ripens approximately 5 weeks earlier and the fruit and leaves are more resistant to "bacterial spot" caused by *Xanthomonas pruni* and in comparison to its pollen parent Crimson Gold Nectarine (U.S. Plant Pat. No. 2,825) the fruit of the new variety is larger in size and ripens approximately 7 days later.

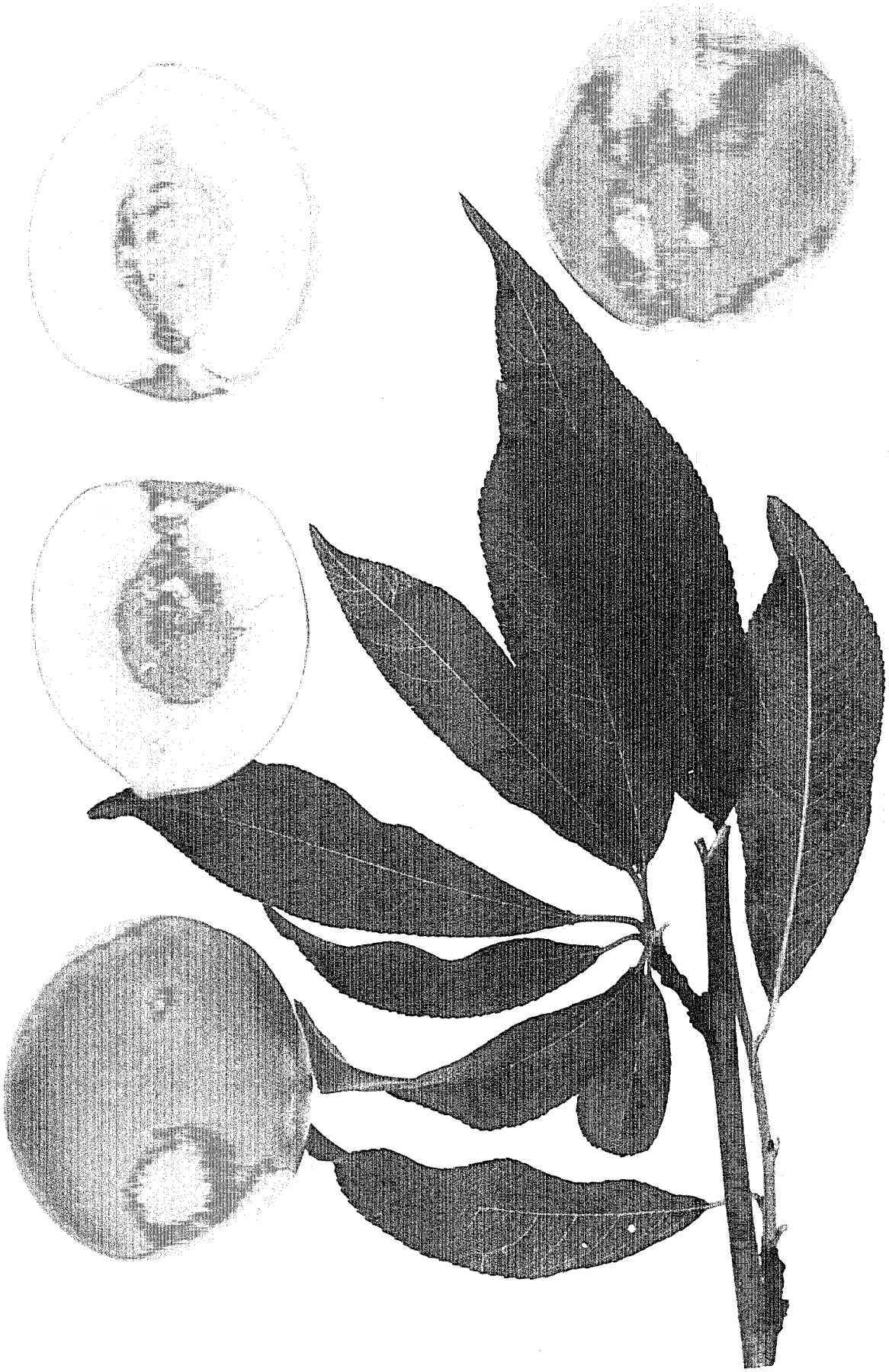

* * * * *